(12) United States Patent
Saikley et al.

(10) Patent No.: US 8,079,961 B2
(45) Date of Patent: Dec. 20, 2011

(54) AUTOMATIC BIOLOGICAL ANALYTE TESTING METER WITH INTEGRATED LANCING DEVICE AND METHODS OF USE

(75) Inventors: Charles R. Saikley, Alameda, CA (US); Paul R. Hamerton-Kelly, Lake Oswego, OR (US); Sophia Sia, Union City, CA (US); Daniel F. Kennedy, San Francisco, CA (US); Matthew W. Peterson, San Francisco, CA (US); Sammy Cheuksang Tsang, San Francisco, CA (US); W. Mark Lortz, Pleasanton, CA (US); Joseph A. Vivolo, San Francisco, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 238 days.

(21) Appl. No.: 12/490,218

(22) Filed: Jun. 23, 2009

(65) Prior Publication Data
US 2009/0259147 A1    Oct. 15, 2009

Related U.S. Application Data

(63) Continuation of application No. 10/701,993, filed on Nov. 4, 2003, now Pat. No. 7,572,237.

(60) Provisional application No. 60/424,414, filed on Nov. 6, 2002.

(51) Int. Cl.
*A61B 5/00* (2006.01)
*B65D 81/00* (2006.01)

(52) U.S. Cl. ........................ 600/583; 600/573

(58) Field of Classification Search .................. 600/300, 600/322, 573, 576, 577, 578, 579, 580, 582, 600/583, 584; 606/167, 181, 182, 183
See application file for complete search history.

(56) References Cited

U.S. PATENT DOCUMENTS

| | | | |
|---|---|---|---|
| 4,210,156 | A | 7/1980 | Bennett |
| D264,378 | S | 5/1982 | Thomas et al. |
| 4,414,975 | A | 11/1983 | Ryder et al. |
| 4,416,279 | A | 11/1983 | Lindner et al. |
| 4,439,197 | A | 3/1984 | Honda et al. |
| 4,449,529 | A | 5/1984 | Burns et al. |

(Continued)

FOREIGN PATENT DOCUMENTS
EP    0 885 590 A1    12/1998
(Continued)

*Primary Examiner* — Jeffrey G Hoekstra
(74) *Attorney, Agent, or Firm* — Edward J. Baba; Bozicevic, Field & Francis LLP

(57) ABSTRACT

The invention is directed to an integrated device for sampling and testing an analyte. The device generally comprises a housing, a lancing device for sampling an analyte, a test strip for substantially capturing at least a portion of the analyte, and a display unit for displaying a result corresponding to the captured portion of the analyte. The invention is further directed to methods for sampling and testing. For example, one method comprises performing a single operation to sample an analyte, to capture the sampled analyte, to perform testing on the sampled analyte, and to display a result corresponding to the performed test. A method such as this can be carried out using an integrated sampling and testing device of the invention, for example, by placing the device the device on a test site of a subject, such as a patient, and performing the single operation to obtain a test result. The invention has particular application in the sampling and testing of analytes in blood, such as the blood of a diabetic patient.

16 Claims, 13 Drawing Sheets

U.S. PATENT DOCUMENTS

| | | | |
|---|---|---|---|
| 4,452,243 A | 6/1984 | Leopoldi et al. |
| 4,503,856 A | 3/1985 | Cornell et al. |
| 4,517,978 A | 5/1985 | Levin et al. |
| 4,538,271 A | 8/1985 | Kohs |
| 4,539,988 A | 9/1985 | Shirley et al. |
| 4,577,630 A | 3/1986 | Nitzsche et al. |
| 4,580,564 A | 4/1986 | Andersen |
| 4,608,997 A | 9/1986 | Conway |
| 4,627,445 A | 12/1986 | Garcia et al. |
| 4,637,403 A | 1/1987 | Garcia et al. |
| 4,648,408 A | 3/1987 | Hutchinson et al. |
| 4,653,513 A | 3/1987 | Dombrowski |
| 4,658,821 A | 4/1987 | Chiodo et al. |
| 4,677,979 A | 7/1987 | Burns |
| 4,715,374 A | 12/1987 | Maggio |
| D297,978 S | 10/1988 | White |
| 4,787,398 A | 11/1988 | Garcia et al. |
| 4,844,095 A | 7/1989 | Chiodo et al. |
| 4,856,515 A | 8/1989 | Turner et al. |
| 4,869,249 A | 9/1989 | Crossman et al. |
| 4,891,319 A | 1/1990 | Roser |
| 4,895,147 A | 1/1990 | Bodicky et al. |
| 4,920,977 A | 5/1990 | Haynes |
| 4,924,879 A | 5/1990 | O'Brien |
| 4,963,814 A | 10/1990 | Parks et al. |
| 4,994,068 A | 2/1991 | Hugnagle |
| 4,999,582 A | 3/1991 | Parks et al. |
| 4,999,632 A | 3/1991 | Parks |
| 5,053,199 A | 10/1991 | Keiser et al. |
| 5,079,920 A | 1/1992 | Whitehead et al. |
| 5,086,780 A | 2/1992 | Schmitt |
| 5,100,427 A | 3/1992 | Crossman et al. |
| 5,100,428 A | 3/1992 | Mumford |
| 5,108,564 A | 4/1992 | Szuminsky et al. |
| 5,128,015 A | 7/1992 | Szuminsky et al. |
| 5,152,775 A | 10/1992 | Ruppert |
| 5,201,324 A | 4/1993 | Swierczek |
| 5,206,147 A | 4/1993 | Hoenes |
| 5,207,666 A | 5/1993 | Idriss et al. |
| 5,217,480 A | 6/1993 | Haber et al. |
| 5,240,860 A | 8/1993 | Hoenes et al. |
| D342,573 S | 12/1993 | Cerola |
| 5,279,294 A | 1/1994 | Anderson et al. |
| 5,288,636 A | 2/1994 | Pollmaim et al. |
| 5,318,583 A | 6/1994 | Rabenau et al. |
| 5,318,584 A | 6/1994 | Lange et al. |
| 5,324,303 A | 6/1994 | Strong et al. |
| 5,334,508 A | 8/1994 | Hoenes |
| 5,352,351 A | 10/1994 | White et al. |
| 5,366,609 A | 11/1994 | White et al. |
| 5,382,523 A | 1/1995 | Hoenes et al. |
| 5,405,511 A | 4/1995 | White et al. |
| 5,424,035 A | 6/1995 | Hoenes et al. |
| 5,454,828 A | 10/1995 | Schraga |
| 5,463,467 A | 10/1995 | Baumann et al. |
| 5,464,418 A | 11/1995 | Schraga |
| 5,487,748 A | 1/1996 | Marshall et al. |
| 5,504,011 A | 4/1996 | Gavin et al. |
| 5,508,171 A | 4/1996 | Walling et al. |
| 5,510,266 A | 4/1996 | Bonner et al. |
| 5,518,006 A | 5/1996 | Mawhirt et al. |
| 5,521,060 A | 5/1996 | Hoenes et al. |
| 5,554,166 A | 9/1996 | Lange et al. |
| 5,568,806 A | 10/1996 | Cheney, II et al. |
| 5,575,403 A | 11/1996 | Charlton et al. |
| 5,582,697 A | 12/1996 | Ikeda et al. |
| 5,586,553 A | 12/1996 | Halili et al. |
| D378,233 S | 2/1997 | Warner |
| 5,622,413 A | 4/1997 | Kim et al. |
| 5,622,482 A | 4/1997 | Lee |
| 5,627,075 A | 5/1997 | Bateson |
| 5,630,986 A | 5/1997 | Charlton et al. |
| 5,632,410 A | 5/1997 | Moulton et al. |
| 5,660,791 A | 8/1997 | Brenneman et al. |
| 5,666,966 A | 9/1997 | Horie et al. |
| 5,708,247 A | 1/1998 | McAleer et al. |
| 5,709,699 A | 1/1998 | Warner |
| 5,720,924 A | 2/1998 | Eikmeier et al. |
| 5,730,753 A | 3/1998 | Morita |
| 5,733,300 A | 3/1998 | Pambianchi et al. |
| 5,738,244 A | 4/1998 | Charlton et al. |
| 5,743,861 A | 4/1998 | Columbus et al. |
| 5,786,584 A | 7/1998 | Button et al. |
| 5,810,199 A | 9/1998 | Charlton et al. |
| 5,846,837 A | 12/1998 | Thym et al. |
| 5,863,800 A | 1/1999 | Eikmeier et al. |
| 5,913,868 A | 6/1999 | Marshall et al. |
| 5,916,230 A | 6/1999 | Brenneman et al. |
| RE36,268 E | 8/1999 | Szuminsky et al. |
| D412,985 S | 8/1999 | Weekes |
| 5,938,679 A | 8/1999 | Freeman et al. |
| 5,947,957 A | 9/1999 | Morris |
| 5,951,492 A | 9/1999 | Douglas et al. |
| 5,951,836 A | 9/1999 | McAleer et al. |
| 5,954,643 A | 9/1999 | VanAntwerp et al. |
| 5,971,941 A | 10/1999 | Simons et al. |
| 5,984,940 A | 11/1999 | Davis et al. |
| 5,997,817 A | 12/1999 | Crismore et al. |
| D418,917 S | 1/2000 | Duchon et al. |
| 6,022,366 A | 2/2000 | Schraga |
| 6,027,459 A | 2/2000 | Shain et al. |
| 6,036,919 A | 3/2000 | Thym et al. |
| 6,036,924 A | 3/2000 | Simons et al. |
| 6,053,930 A | 4/2000 | Ruppert |
| 6,055,060 A | 4/2000 | Bolduan et al. |
| 6,059,546 A | 5/2000 | Brenan et al. |
| 6,063,039 A | 5/2000 | Cunningham et al. |
| D427,312 S | 6/2000 | Douglas |
| 6,071,249 A | 6/2000 | Cunningham et al. |
| 6,071,251 A | 6/2000 | Cunningham et al. |
| D428,150 S | 7/2000 | Ruf et al. |
| 6,085,871 A | 7/2000 | Karamata |
| 6,090,124 A | 7/2000 | Weekes |
| 6,093,156 A | 7/2000 | Cunningham et al. |
| D429,814 S | 8/2000 | Lorwald et al. |
| 6,099,484 A | 8/2000 | Douglas et al. |
| 6,106,537 A | 8/2000 | Crossman et al. |
| 6,136,013 A | 10/2000 | Marshall et al. |
| 6,143,164 A | 11/2000 | Heller et al. |
| 6,149,608 A | 11/2000 | Marshall et al. |
| 6,156,051 A | 12/2000 | Schraga |
| 6,190,398 B1 | 2/2001 | Schraga |
| 6,192,891 B1 | 2/2001 | Gravel et al. |
| 6,206,841 B1 | 3/2001 | Cunningham et al. |
| 6,210,420 B1 | 4/2001 | Mauze et al. |
| 6,267,722 B1 | 7/2001 | Anderson et al. |
| 6,283,926 B1 | 9/2001 | Cunningham et al. |
| 6,283,982 B1 | 9/2001 | Levaughn et al. |
| 6,299,757 B1 | 10/2001 | Feldman et al. |
| 6,306,104 B1 | 10/2001 | Cunningham et al. |
| 6,306,152 B1 | 10/2001 | Verdonk et al. |
| 6,346,114 B1 | 2/2002 | Schraga |
| 6,352,514 B1 | 3/2002 | Douglas et al. |
| 6,368,141 B1 | 4/2002 | VanAntwerp et al. |
| 6,409,740 B1 | 6/2002 | Kuhr et al. |
| 6,506,168 B1 | 1/2003 | Fathallah et al. |
| 6,616,819 B1 | 9/2003 | Llamos et al. |
| 2003/0028125 A1 | 2/2003 | Yuzhakov et al. |
| 2003/0143113 A2 | 7/2003 | Yuzhakov et al. |
| 2003/0191415 A1 | 10/2003 | Moerman et al. |
| 2003/0198558 A1 | 10/2003 | Nason et al. |
| 2004/0002682 A1 | 1/2004 | Kovelman et al. |

FOREIGN PATENT DOCUMENTS

| | | | |
|---|---|---|---|
| EP | 1 031 318 A1 | 8/2000 |
| EP | 1 060 707 A2 | 12/2000 |
| EP | 1 101 443 A2 | 5/2001 |
| EP | 1 132 103 A1 | 9/2001 |
| EP | 1 101 443 A3 | 1/2002 |
| JP | 4-194660 | 7/1992 |
| WO | WO 86/00513 | 1/1986 |
| WO | WO 01/64105 A1 | 9/2001 |
| WO | WO 01/72220 A1 | 10/2001 |
| WO | WO 01/73395 A2 | 10/2001 |
| WO | WO 03/082091 A2 | 10/2003 |

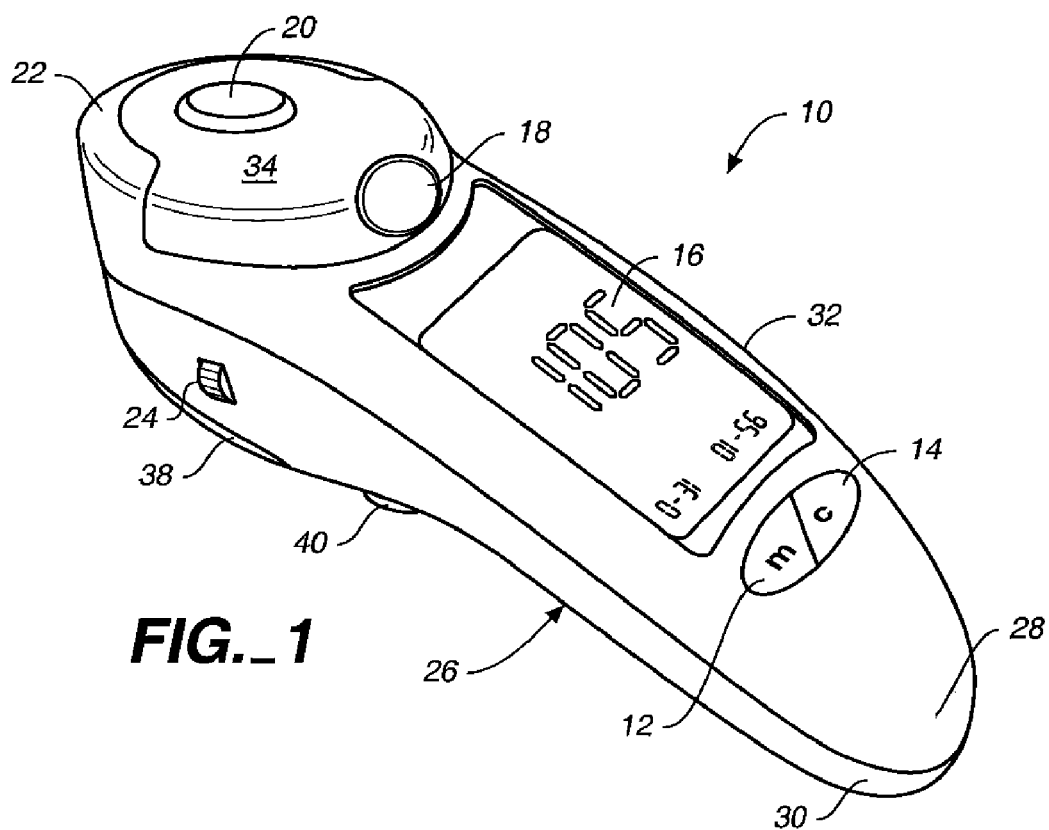
FIG._1
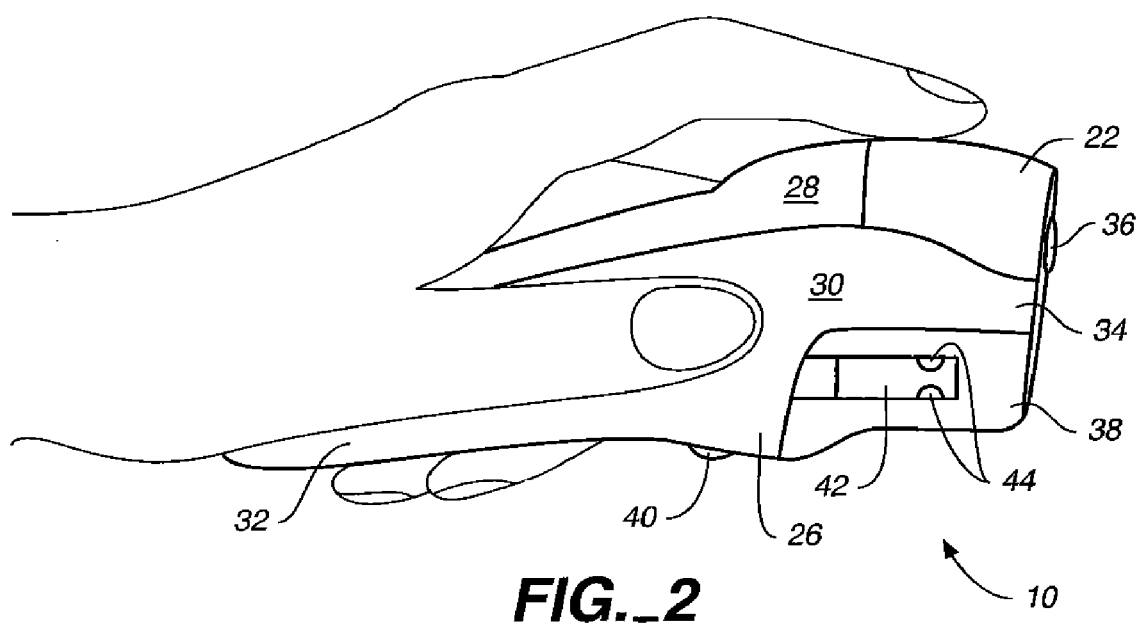
FIG._2

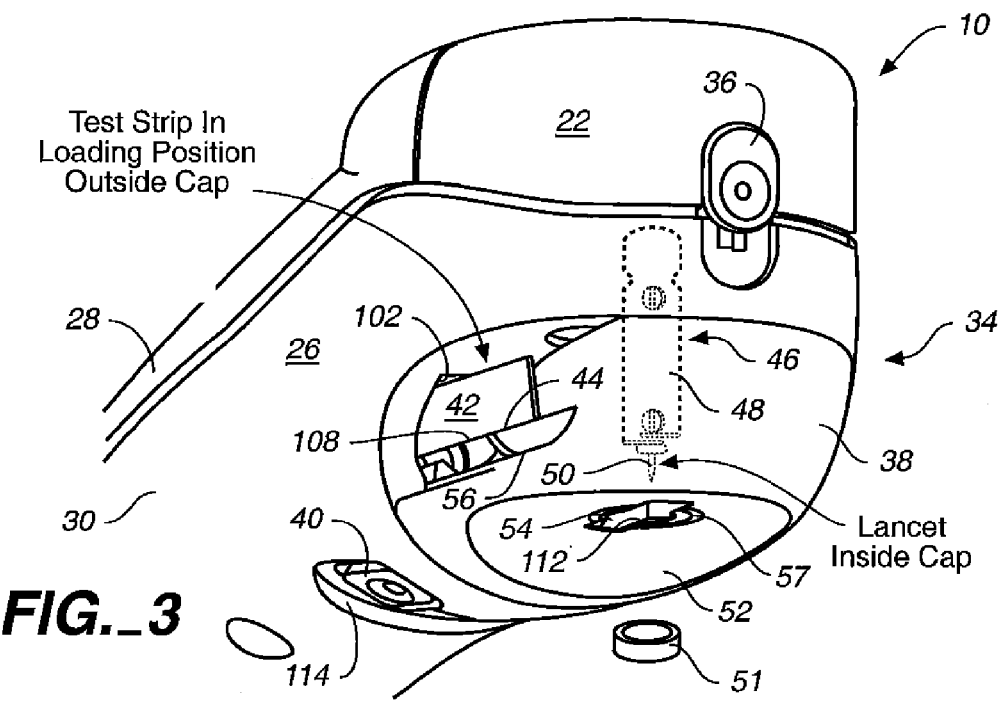
FIG._3
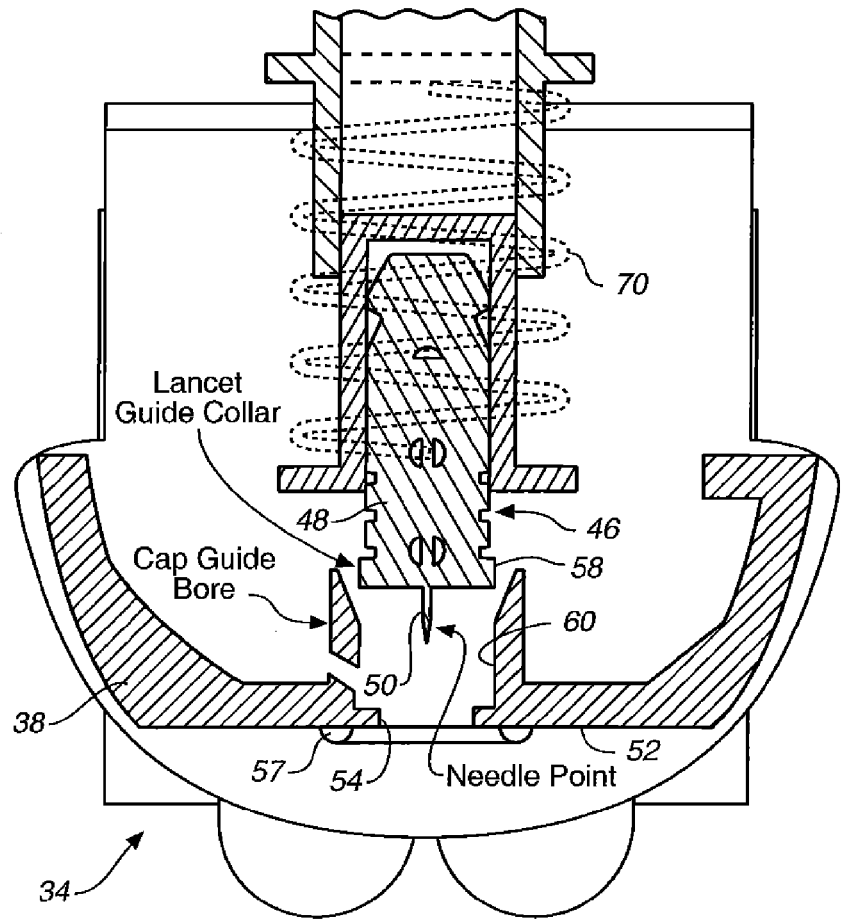
FIG._4

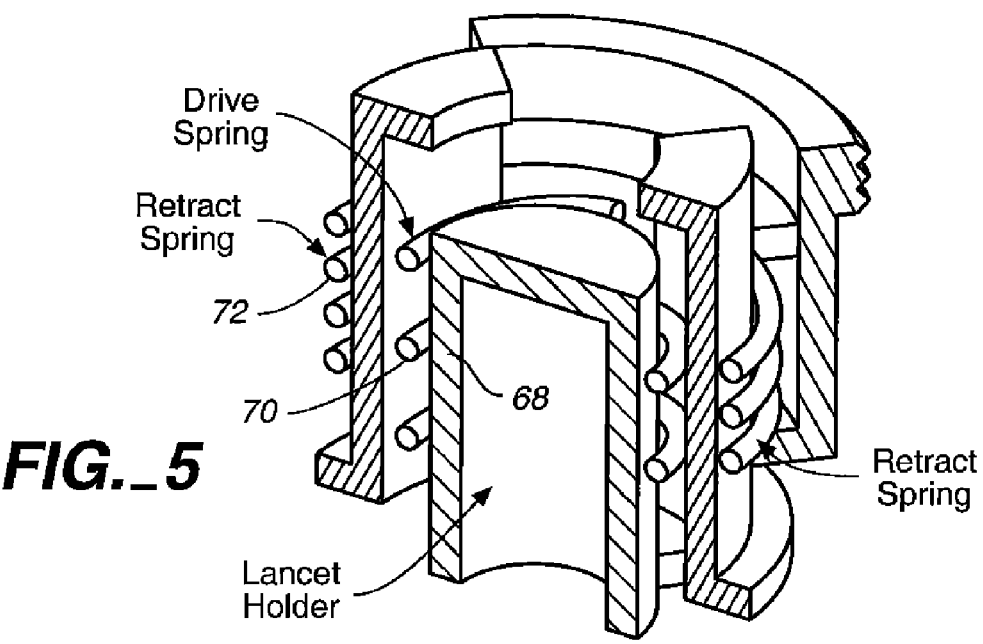
FIG._5
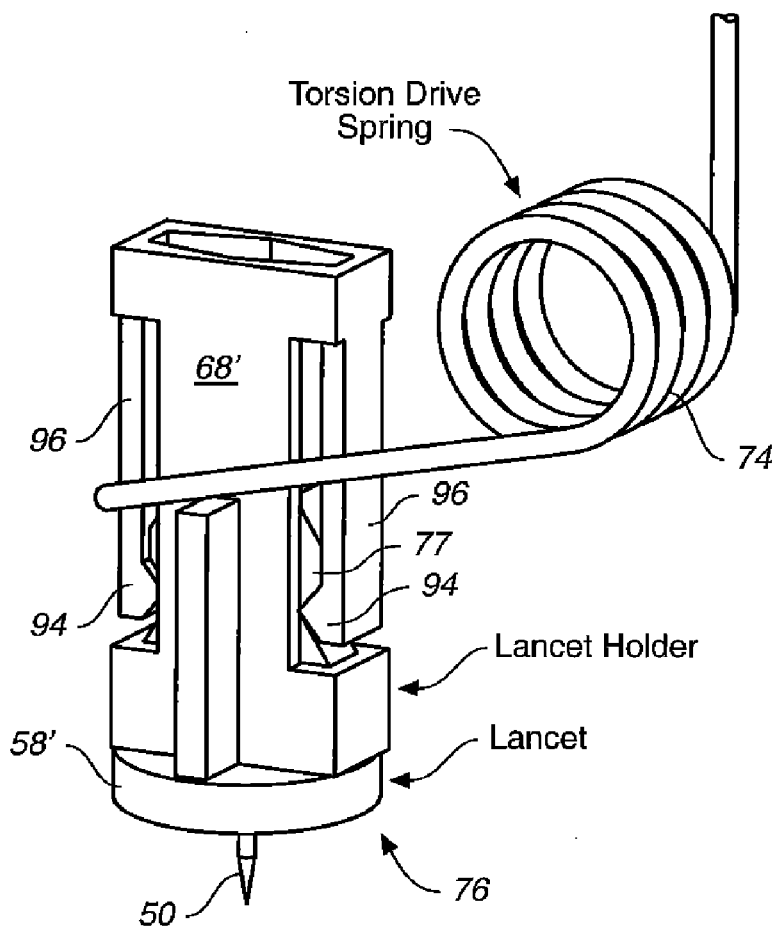
FIG._6

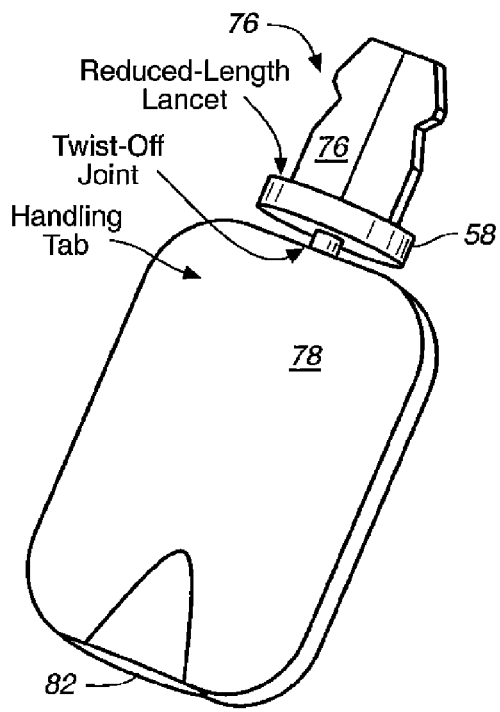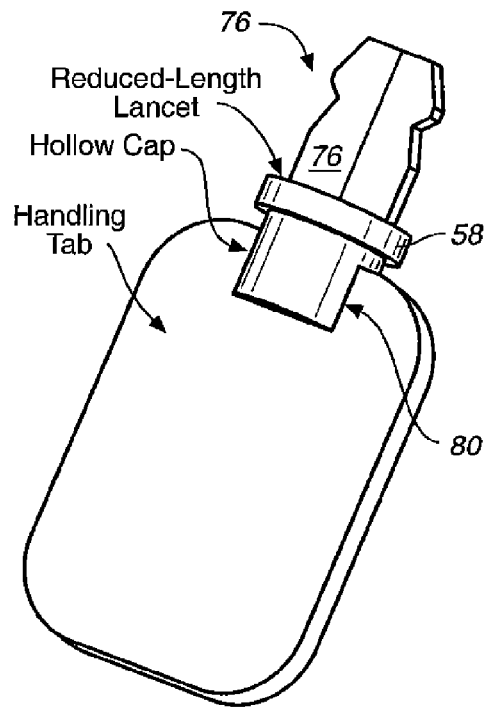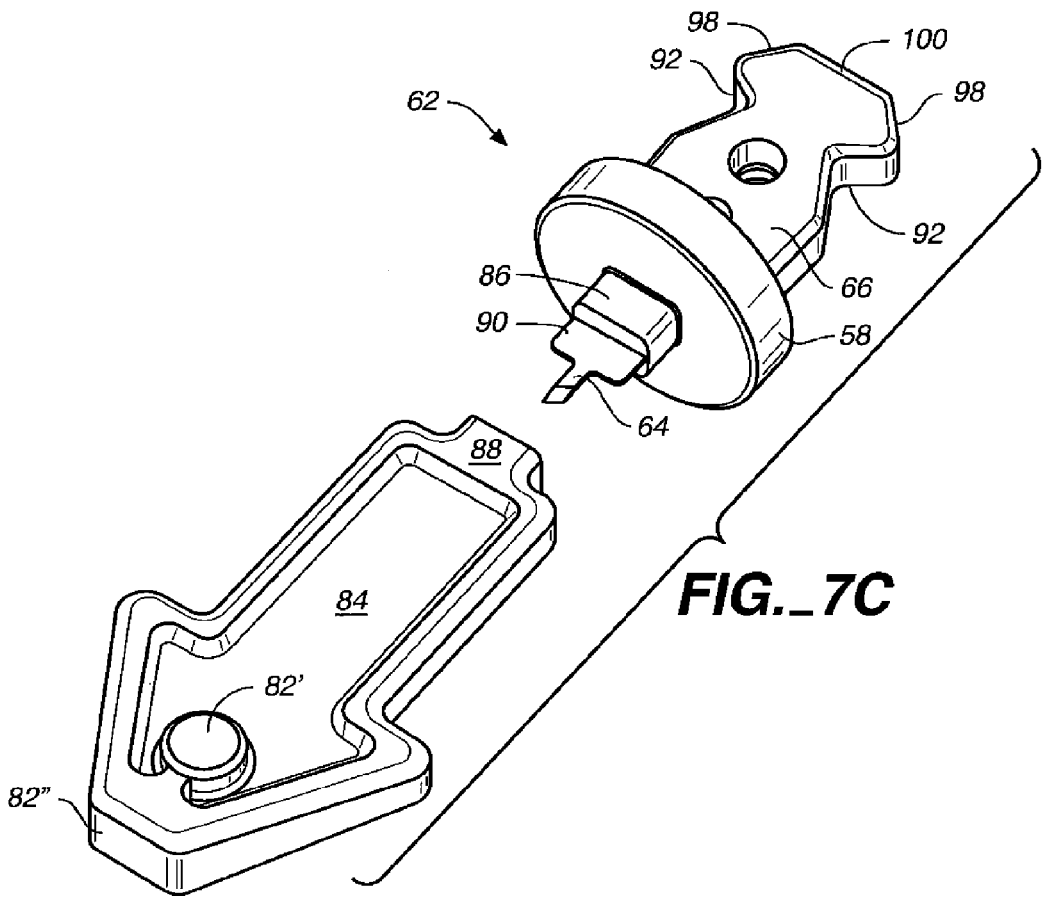

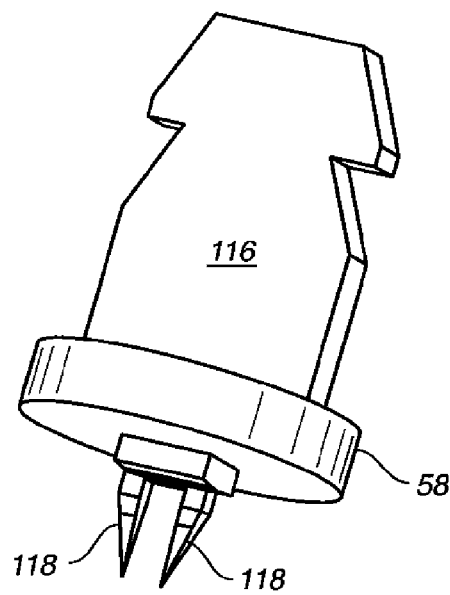
FIG._7D
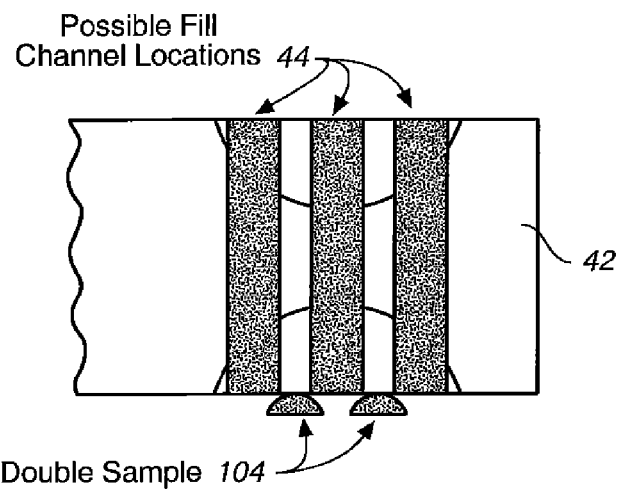
FIG._7E
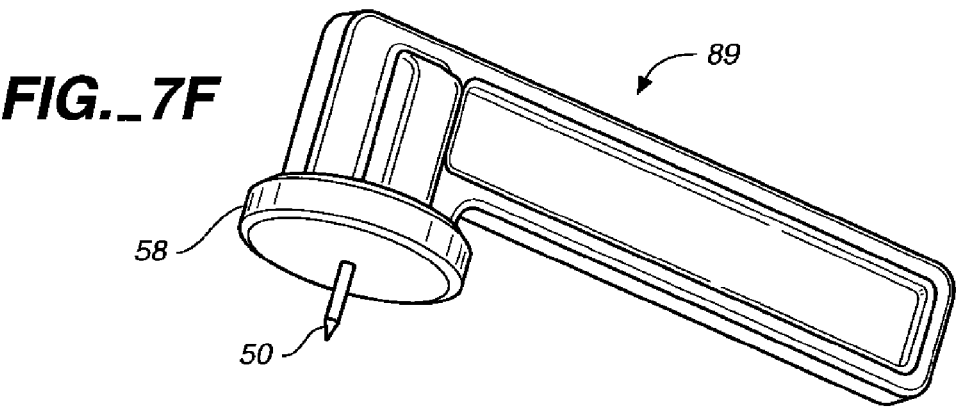
FIG._7F

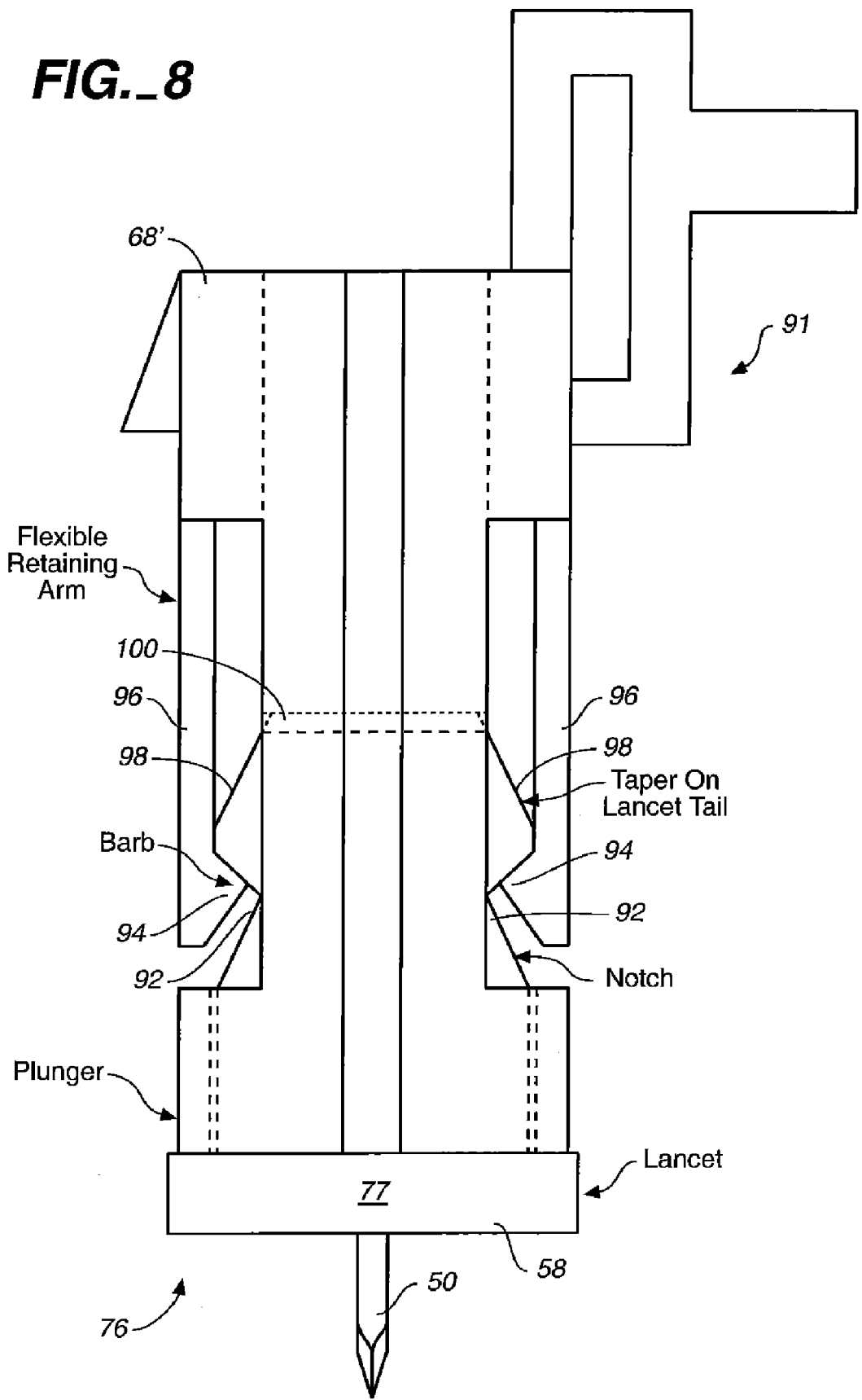

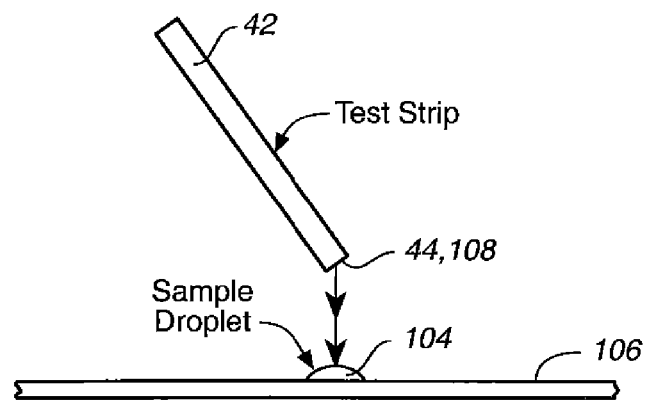
FIG._9A
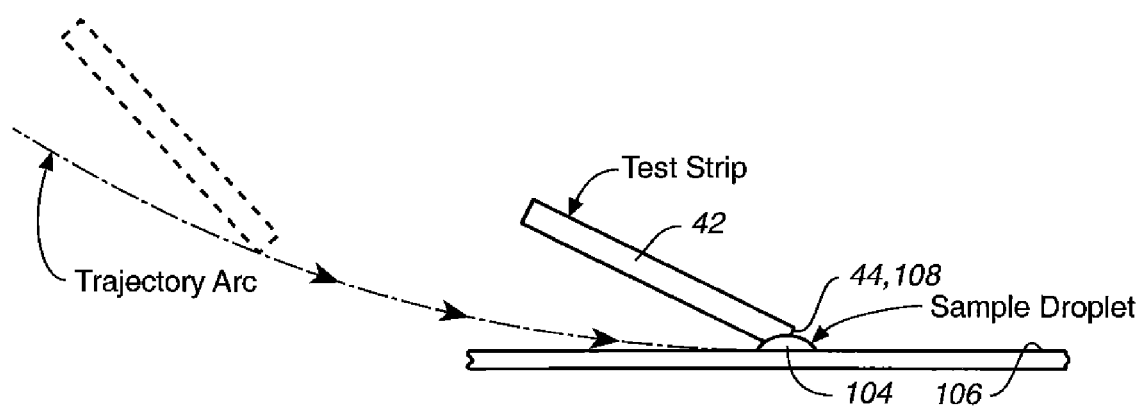
FIG._9B

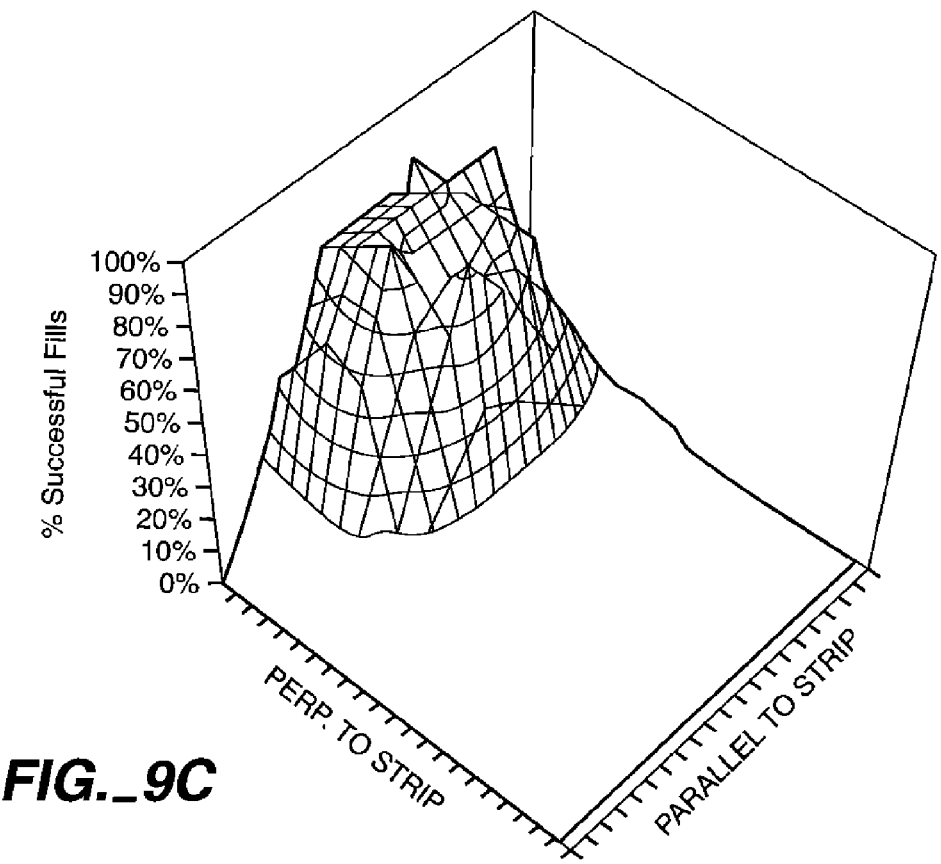
*FIG._9C*
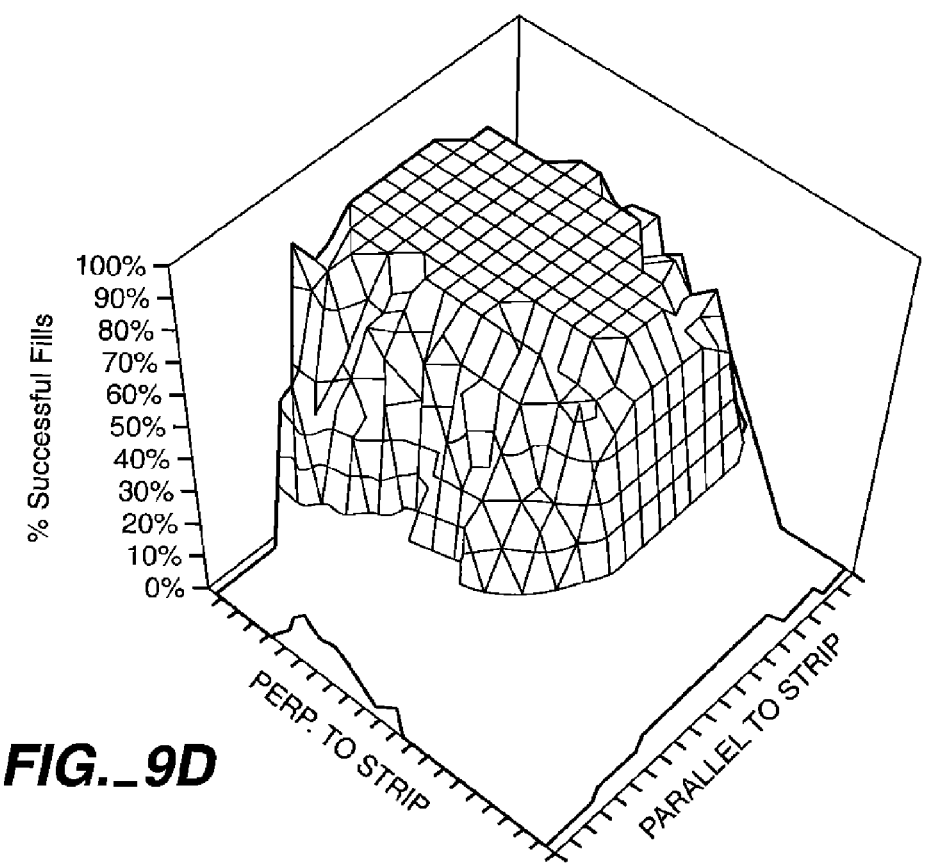
*FIG._9D*

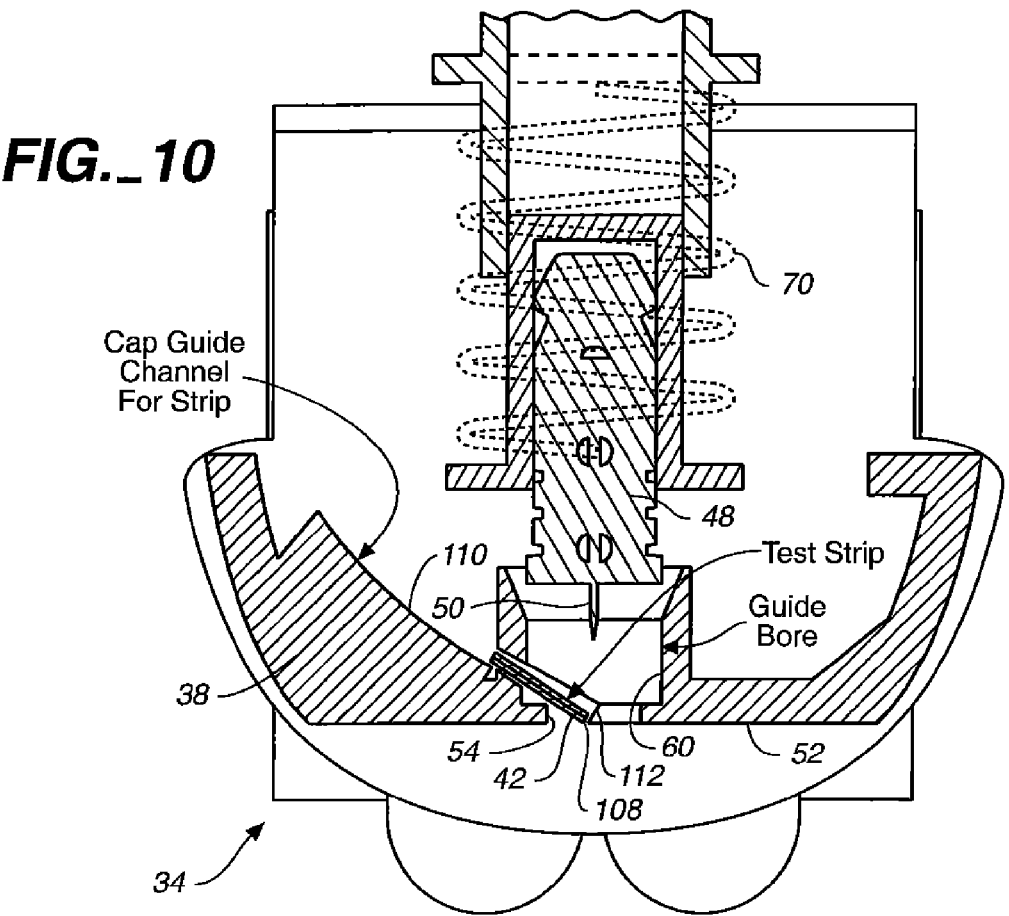
FIG._10
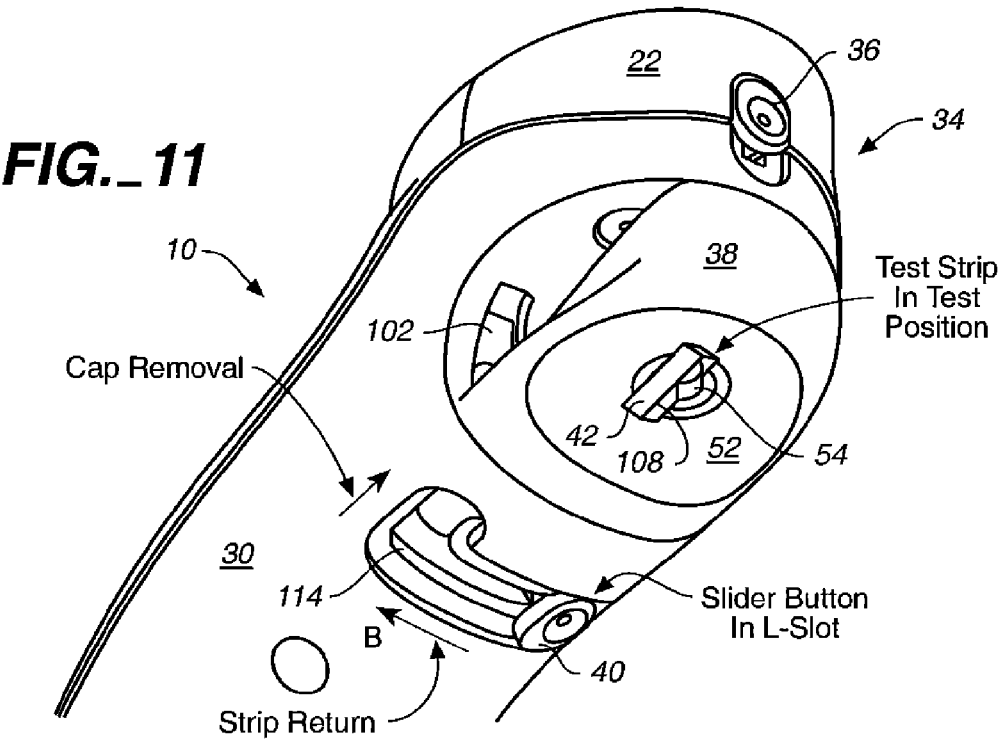
FIG._11

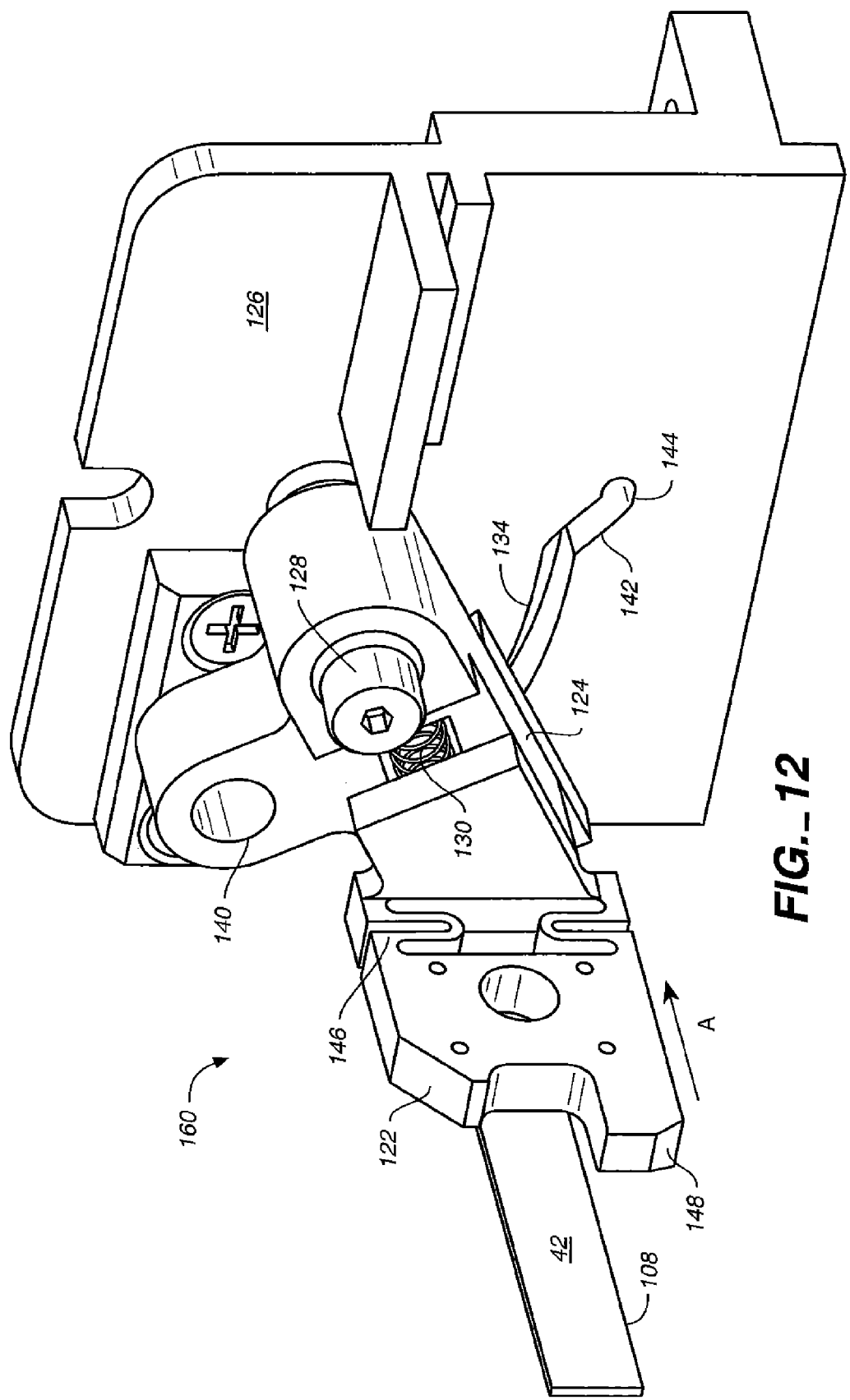
FIG._12

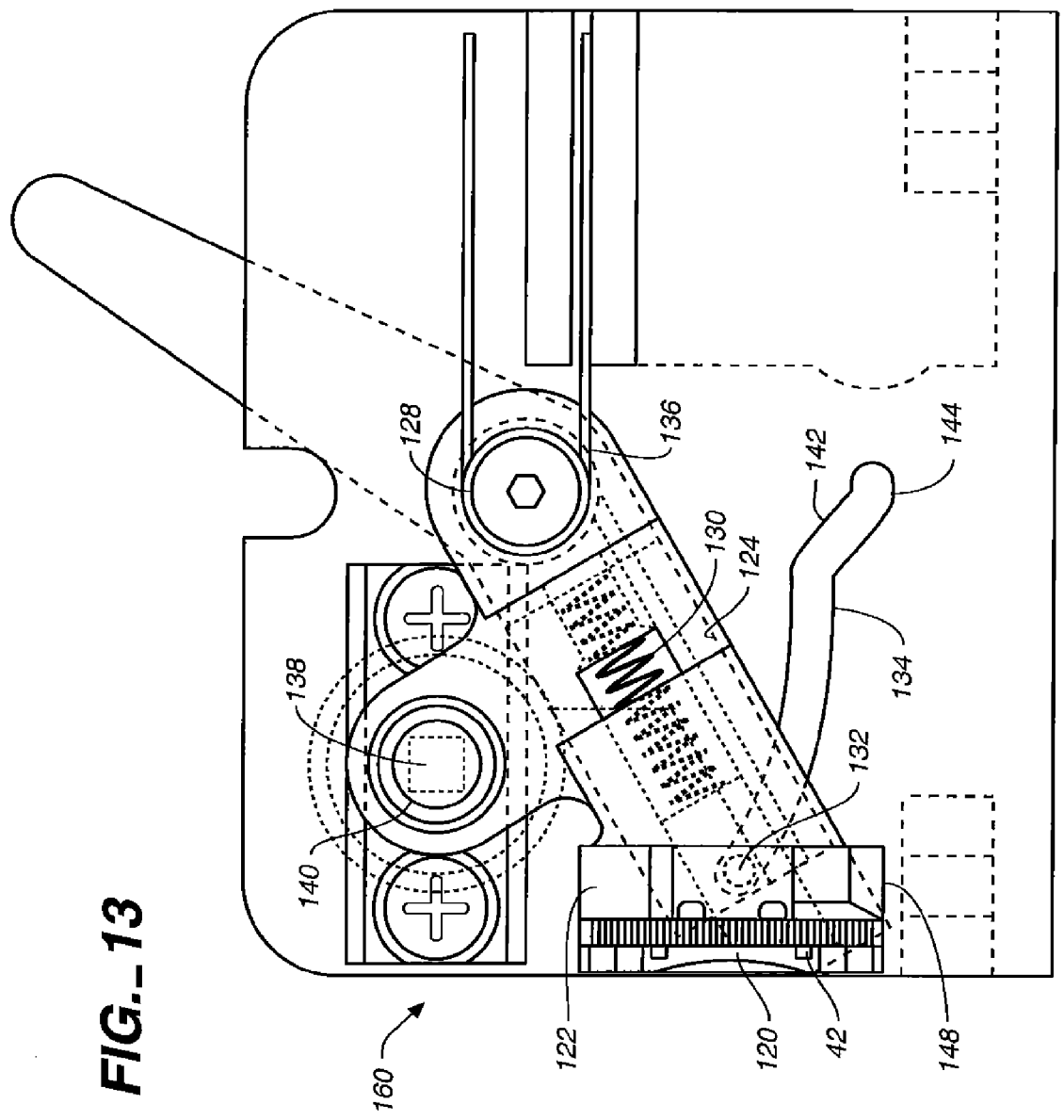
FIG._13

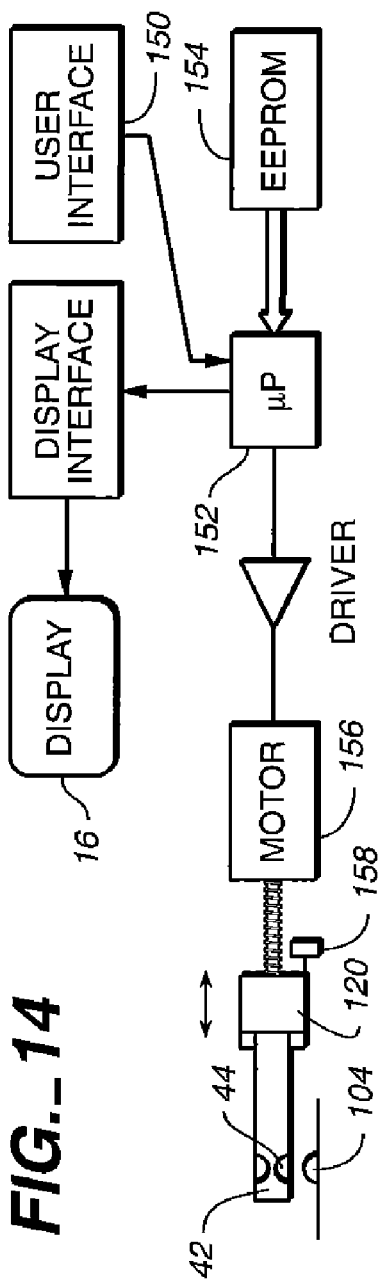
FIG._14
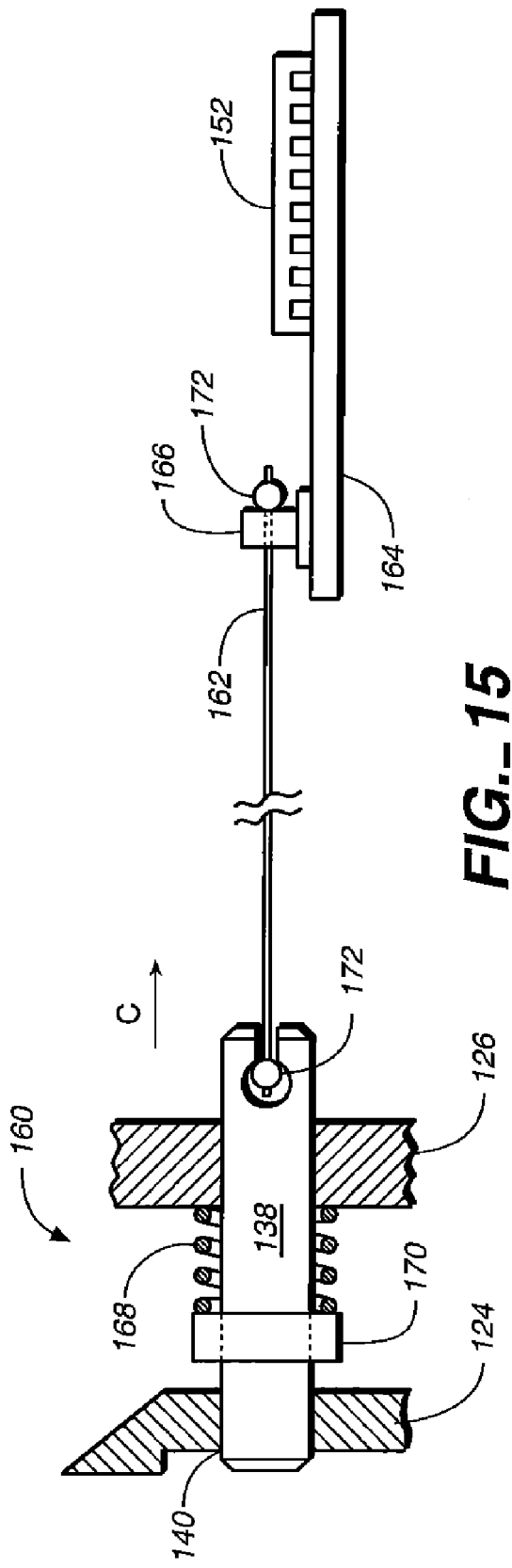
FIG._15

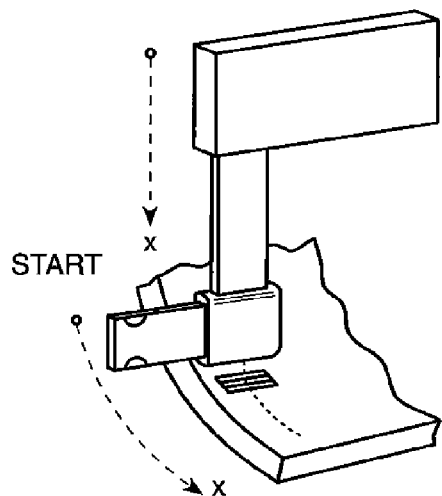
FIG._16A
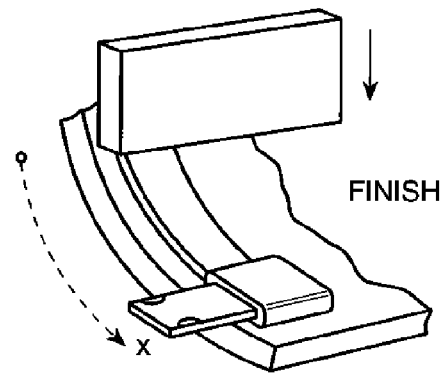
FIG._16B
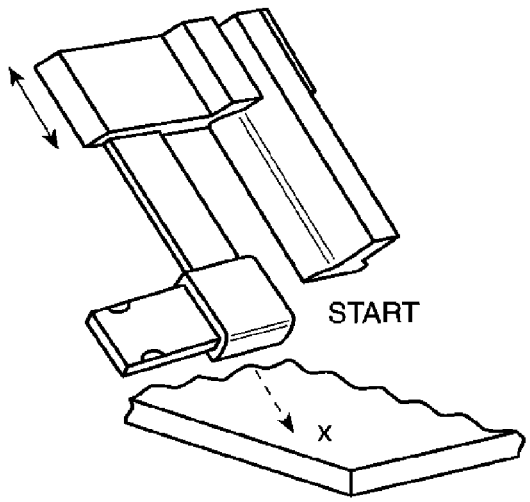
FIG._17A
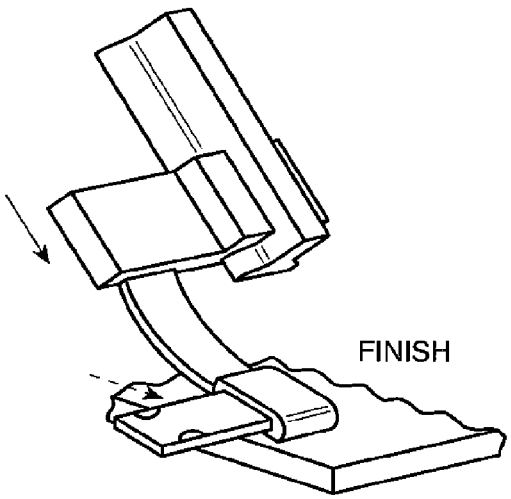
FIG._17B
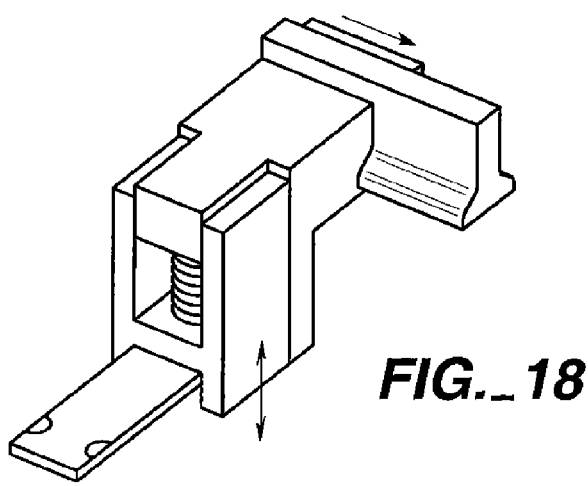
FIG._18

AUTOMATIC BIOLOGICAL ANALYTE TESTING METER WITH INTEGRATED LANCING DEVICE AND METHODS OF USE

CROSS-REFERENCE TO RELATED APPLICATION

This non-provisional application is a continuation of U.S. Application Ser. No. 10/701,993, filed Nov. 4, 2003, now issued as U.S. Pat. No. 7,572,237, which claims priority based on U.S. Provisional Application No. 60/424,414, entitled "Automatic Biological Analyte Testing Meter with Integrated Lancing Device and Methods of Use," filed on Nov. 6, 2002, which are incorporated herein in their entirety by this reference.

FIELD OF THE INVENTION

In general, this invention relates to skin lancing devices, analyte sensors and analysis meters for determining biological analyte levels, and more specifically, a portable device that integrates the functions of these separate devices in a single unit.

BACKGROUND OF THE INVENTION

Methods and devices used by a patient to measure a bioanalyte are well known in the art. For example, currently available technology allows a diabetic patient to monitor his own blood glucose level by drawing a blood sample with a lancing device, using an electrochemical sensor strip to capture the blood sample, and using an electronic meter connected to the sensor strip to analyze the blood sample and display the result. Until recently, relatively large sample volumes were required to be drawn, generally 3 microliters or more of blood or other biological fluid. These fluid samples are obtained from a patient, for example, using a needle and syringe, or by lancing a portion of the skin such as the fingertip and "milking" the area to obtain a useful sample volume. These procedures are inconvenient for the patient, and often painful, particularly when frequent samples are required. Less painful methods for obtaining a sample are known such as lancing the arm or thigh, which have lower nerve ending density. However, lancing the body in these preferred regions typically produces submicroliter samples of blood, because these regions are not heavily supplied with near-surface capillary vessels. The recently introduced FreeStyle™ Blood Glucose Monitoring System developed by TheraSense, Inc. of Alameda, Calif., is capable of consistently, accurately and precisely measuring sample sizes of only ⅓ microliter using this preferred "alternate site testing" (AST). U.S. Patent No. 6,299,757, issued Oct. 9, 2001 to TheraSense, Inc. and incorporated herein by reference describes the construction and operation of the above FreeStyle system. U.S. Pat. No. 6,283,982 issued Sep. 4, 2001 to TheraSense, Inc. and incorporated herein by reference describes a lancing device that is used in the FreeStyle system.

A ⅓ microliter sample is about the size of a pinhead. Elderly patients and those with reduced eyesight and dexterity can have problems seeing and capturing such a small sample. Current testing procedures involving a lancing device, disposable lancets, meter and disposable test strips involve a lot of steps. It can be difficult for patients to remember all the steps and their proper order. Active patients testing outdoors, for example, can have a tough time juggling all of the different pieces during a test. Also, younger patients want to be able to quickly and discreetly test themselves without drawing attention with a lot of paraphernalia and testing steps.

What is needed and has not been provided by the prior art is a simpler testing method using a compact, unitary testing device.

SUMMARY OF THE INVENTION

The testing instrument of the present invention provides a method for obtaining a sample and testing that sample using a single device. Further, the instrument automatically performs all the testing steps in the proper order with the proper delays for each. The entire testing process is initiated by the patient with a single press of a button. The instrument automatically inserts and retracts a lancet into the skin with the proper speed and force, waits a predetermined time for a fluid sample to form on the skin, aligns the fill channel of a test strip with the small fluid sample and brings the two into contact to capture the sample, indicates to the patient when a sufficient sample has been captured, waits for electrochemical testing of the sample to be complete, displays the test result to the patient, and records all of the test results for later review, analysis and/or uploading to a computer network.

BRIEF DESCRIPTION OF THE DRAWINGS

FIG. 1 is a top perspective view showing a unitary lancing device, test strip applicator and testing meter constructed according to the present invention.

FIG. 2 is a side elevation view showing the unitary handheld instrument of FIG. 1.

FIG. 3 is a bottom perspective view schematically showing the cap, test strip and lancet on the instrument of FIG. 1.

FIG. 4 is a front cross-sectional view schematically showing lancet positioning features.

FIG. 5 is broken away perspective view schematically showing a concentric spring lancing mechanism.

FIG. 6 is a perspective view schematically showing a torsion spring lancing mechanism.

FIG. 7A is a perspective view of a first embodiment of an inventive lancet and cap combination.

FIG. 7B is a perspective view of a second embodiment of an inventive lancet and cap combination.

FIG. 7C is a perspective view of a third embodiment of an inventive lancet and cap combination.

FIG. 7D is a perspective view of a multi-pointed lancet.

FIG. 7E is a schematic view showing possible locations of test strip fill channels in relation to fluid samples created by the lancet of FIG. 7D.

FIG. 7F is a perspective view of a right-angle lancet.

FIG. 8 is a side elevation view schematically showing a lancet retention and ejection mechanism.

FIG. 9A is a front elevation view schematically showing a vertical test trip trajectory.

FIG. 9B is a front elevation view schematically showing an arcuate test trip trajectory.

FIG. 9C is a graph showing blood sample location versus fill success rate for vertical trajectory test strips.

FIG. 9D is a graph showing blood sample location versus fill success rate for arcuate trajectory test strips.

FIG. 10 is a front cross-sectional view schematically showing test strip guiding features.

FIG. 11 is a bottom perspective view schematically showing the strip motion and cap removal interlock on the instrument of FIG. 1.

FIG. 12 is a perspective view of a test strip moving mechanism.

FIG. 13 is a side elevation view of the test strip mechanism of FIG. 12.

FIG. 14 is schematic view showing a test strip fill channel location coding and translation scheme.

FIG. 15 is fragmentary side elevation view showing the use of a Shape Memory Alloy to activate a test strip mechanism similar to that of FIG. 12.

FIG. 16A is a perspective view showing an alternative embodiment of a test strip moving mechanism in the loading position.

FIG. 16B is a perspective view showing an alternative embodiment of a test strip moving mechanism in the testing position.

FIG. 17A is a perspective view showing another alternative embodiment of a test strip moving mechanism in the loading position.

FIG. 17B is a perspective view showing another alternative embodiment of a test strip moving mechanism in the testing position.

FIG. 18 is a perspective view showing yet another alternative embodiment of a test strip moving mechanism.

DETAILED DESCRIPTION OF THE PREFERRED EMBODIMENTS

Referring to FIG. 1, an integrated device 10 is shown that functions as an automatic lancing device, test strip applicator and testing meter. Integrated device 10 includes function buttons 12 and 14, liquid crystal display 16, display backlight button 18, actuator button 20, cocking collar 22 and lancing depth control thumbwheel 24. Preferably device 10 has a plastic housing 26 having upper shell 28 and lower shell 30, forming a main body portion 32 and head portion 34.

Referring to FIG. 2, integrated device 10 has a lancet ejection lever 36, a clear protective cap 38, and a strip return and cap removal lever 40. Disposable electrochemical test strip 42 with side fill channels 44 is shown in the loading position. The construction and manual use of a side-file test strip 42 is fully described in U.S. Pat. No. 6,338,790 issued on Jan. 15, 2002 to TheraSense, Inc., and U.S. application Ser. No. 09/434,026, filed Nov. 9, 1999, both incorporated herein by reference. Preferably, an existing test strip, such as the FreeStyle™ brand test strip developed and marketed by TheraSense, Inc., is used with the present invention rather than a propriety format designed especially for the integrated device. Advantages to using existing test strips include utilizing existing research and development, manufacturing, distribution, and inventory systems and having larger economies of scale, thereby allowing for a lower cost test strip. Also, a large user base of patients are already familiar with the existing strips, and if they desire, can alternately use the same strips in existing manual meters and in the automatic device.

Referring to FIG. 3, features of clear protective cap 38 are shown. Also shown is a vertically oriented, disposable lancet 46 having a plastic main body 48, a sharp 50 and removable cap 51 for covering sharp 50 when not in installed in device 10. Device cap 38 has a recess 52, preferably for resting on a patient's arm or leg. In use, the device 10 is held as shown in FIG. 2, and preferably oriented generally above and perpendicular to the arm or leg. Aperture 54 is provided in the bottom of cap 38 for allowing at least the sharp 50 of lancet to pass through to the patient's skin during actuation. Slotted opening 56 is provided in one side of cap 38 to allow test strip 42 to pass from the outside loading position to the inside sample gathering position. Other than these two openings, cap 38 completely surrounds lancet 46 before, during and after testing.

To achieve good lancing results, a pressure applicator ring 57 should be provided around aperture 54. Ring 57 helps provide the proper skin tension and capillary blood pressure to ensure that lancet 46 pierces the skin with minimal pain and a sufficient amount of blood is expressed from the wound. In the preferred embodiment, ring 57 is semi-toroidal in shape, has a major diameter of about 11 millimeters, stands about 2 millimeters off of cap 38, and has a width or minor diameter of about 1 millimeter. It is also advantageous to provide a land 1 to 2 millimeters in width between aperture 54 and ring 57. For best results, ring 57 and the enclosed land should be continuous, but they can also be segmented as shown. For further disclosure of pressure applicator ring design, see U.S. Pat. No. 6,283,982 issued Sep. 4, 2001 to TheraSense, Inc. and entitled "Lancing Device and Method of Sample Collection," incorporated herein by reference.

Lancet Guiding and Puncture Site Location Control

Referring to FIG. 4, the lancing operation of integrated device 10 will be described. Since integrated device 10 is to automatically bring the fill channel opening 44 of a test strip 42 (shown in FIG. 2) into contact with a small blood droplet brought up from a lancet puncture in human skin, the device should have very good control over the location of that puncture. Otherwise the mechanism would have little chance of successfully bringing fill channel 44 to the droplet. Control over the puncture site location is achieved, in part, by controlling the tolerances of mechanical features on lancet 46 and then guiding lancet 46 closely over the few millimeters of its travel immediately before it punctures the skin.

On the plastic lancet body 48 itself, the overall dimensions of some guiding feature, located as close to the puncturing tip as possible, should be held to very close tolerances. Features in device 10 mate closely to this guiding feature, but allow it to slide in the direction of lancet travel, giving tight control over the location of the lancet body 48. The location of the lancet sharp 50 within the plastic lancet body 48 is then carefully controlled with respect to the guiding feature, and finally the point of sharp 50 is located precisely with respect to the outside of sharp 50.

In the embodiment of integrated device 10 shown in FIG. 4, the guiding feature on the lancet 46 is a cylindrical collar 58 about 3 mm from the needle point, concentric with needle 50. The outside diameter of collar 58 is controlled to ±0.05 mm and needle 50 is concentric to the outside diameter of collar 58 within ±0.05 mm. The needle point is created by grinding 3 radially symmetric faces, each canted 10° from the needle circumference toward the axis of needle 50. These faces meet at a common point located on the axis of needle 50 and defining the center of the needle's diameter.

The lancet guiding collar 58 slides inside a cylindrical bore 60 in device 10 preferably with a diametral clearance of no more than 0.13 mm. The lancet collar 58 and bore 60 engage at this close fit only for the final 5 mm of the lancet's travel (starting when the needle point is about 2 mm above the skin surface), as earlier engagement would reduce the kinetic energy of lancet 46 through friction and air pressure.

Referring to FIG. 7C, an alternative lancet 62 having a blade-shaped sharp 64 and plastic body 66 can be used instead of the needle-shaped lancet 46 described above. Testing has shown that bladed lancet 62 may draw more blood than needle lancet 46. More importantly, because of constraints in the insert molding processes in which the metal sharps 50 and 64 are molded within plastic housings 48 and 66, respectively, tighter tolerances between the sharp and outside surface of the lancet housing can be obtained by using bladed lancet 62. This aids in more precisely maintaining the location of the blood drop formed on the skin after lancing, thereby allowing more precise alignment between test strip 42 and the blood droplet for more reliable filling of fill channel 44.

Concentric Spring Lancing Mechanism

Referring to FIG. 5, a first lancet driving and retraction mechanism is shown. Feedback from marketing focus groups shows that customers desire an integrated device having a low profile head. In order to make the head 34 of integrated device 10 as short as possible, the lancet drive mechanism needs to have a short height. A typical drive system is comprised of a drive spring and a retraction spring, often placed in series (a line) or parallel (lying next to each other). In the first mechanism embodiment shown in FIG. 5, lancet 46 is received within lancet holder 68 which is captivated within drive spring 70, which in turn is nested within retraction spring 72. This concentric arrangement minimizes the vertical space the components occupy, and minimizes any eccentric forces that might disturb the predictable linear motion of lancet 46 on firing.

Torsion Spring Lancing Mechanism

Referring to FIG. 6, a second lancet driving mechanism is shown. A typical wound-wire coil spring, such as springs 70 and 72 described above, applies a non-uniform force that depends on the amount it is deflected. It also can compress only to a minimum height determined by the wire diameter and number of coils (solid height). One way to obtain more uniform spring force and avoid the limitations of a spring's solid height is to use a torsion spring 74 to drive lancet holder 68'. Torsion spring 74 can be adjusted for force and travel without significantly affecting the overall mechanism size because the body of the spring does not lie in-line with the rest of the mechanism.

Large Lancet Cap for Handling

Referring to FIGS. 7A, 7B and 7C, alternate embodiments of lancets and caps are shown. Another factor that affects the overall size of the lancing mechanism is the length of the lancet itself. Traditional disposable lancets, such as shown in FIG. 3, have an elongate body 48 and a short cap 51. In order to reduce the profile of device head 34, a shortened lancet 76 can be used that is just long enough to engage lancet holder 68 (shown in FIG. 6.) This short length might make the lancet difficult for the user to handle and install, so the protective cap 78 (that is removed before use) should be made much larger than usual to aid handling. Cap 78 may be an integrally molded, pull-off tab such as shown in FIG. 7A, or may be a hollow cap 80 with large handle molded separately or in the same cavity as lancet 76 and placed over lancet 76 after molding, such as shown in FIG. 7B. A hollow cup or solid "pin cushion" type area 82 can be provided at the opposite end of cap 78, as shown in FIG. 7A, to cover the sharp during removal from the device and disposal.

Referring to FIG. 7C, a lancet 62 having a blade-shaped sharp 64, short body 66 and large cap 84 is shown. Traditional and previously described lancets with needle-shaped sharps have their caps removed by twisting. Twisting off the cap of a bladed lancet would likely damage or move the skin piercing edge, resulting in a painful and/or ineffective lance, or inaccurately placed droplet of blood. To assist patients who may be used to twisting caps off of lancets, non-twist features have been incorporated into lancet 62. First, enlarged cap 84 is formed in the shape of an arrow, reminding patients to pull cap 84 off of lancet 62 rather than twisting. Second, non-circular mating collars 86 and 88 are provided on lancet body 66 and cap 84, respectively. When cap 84 is mated with body 66, these collars 86 and 88 are keyed or aligned with each other. Twisting would cause these non-circular collars 86 and 88 to be misaligned, suggesting that this action should not be undertaken. Third, a widened portion 90 is provided on sharp blade 64 away from the narrow distal end, providing resistance to twisting, or making damage to sharp 64 from twisting unlikely. Widened portion 90 provides other benefits as well, such as acting as a redundant maximum sharp penetration depth control in the event of failure of other depth control measures. Widened portion 90 also aids in fabrication of lancet 62, as this configuration is less susceptible to chattering during grinding.

Lancet cap 84 is also provided with pin-cushion type areas 82' and 82", either of which can be used for receiving sharp 64 after use and prior to disposal. Area 82" offers the advantage of allowing the user to extend cap 84 up into device cap 38 to cover sharp 64 while lancet 62 is still in place in integrated device 10. In this manner, used lancet 62 and cap 84 can be ejected from device 10 together as a unit so that the user need not handle small lancet 62 separately while trying to align it with cap 84.

Bladed Lancet Oriented Parallel to Strip

If the width of the cutting edge of sharp 64 is such that it creates an oblong rather than circular blood droplet footprint, the cutting edge should be aligned parallel to test strip 42 (i.e. parallel to the axis of device 10) rather than perpendicular to it, since this is the critical alignment axis, as will be described later. The flat shape of lancet body 66 allows for such alignment and prevents misalignment.

Multi-Pointed Sharp

Referring to FIG. 7D a lancet 116 having a multi-pointed sharp is disclosed. In this embodiment the lancet has two points 118, although in other embodiments (not shown) three or more points 118 could be arranged inline or in other patterns. Each point 118 creates its own skin puncture and blood droplet 104. (Two blood droplets 104, if they are spaced closely together and/or become large enough, may merge into a single oblong or round blood drop.) If integrated device 10 is arranged so that points 118 are aligned parallel to strip 42, the blood droplet 104 and fill channel 44 positioning shown in FIG. 7E results. As shown, the longitudinal position of fill channel 44 relative to blood droplets 104 can be widely varied while still maintaining enough contact with at least one blood droplet 104 to cause fill channel 44 to wick up sufficient blood. Therefore, the use of a multi-pointed sharp allows the positional tolerances of strip 42 and/or lancing to be relaxed while improving strip fill performance.

Right-Angle Lancet

Referring to FIG. 7F, a right-angle lancet 89 is disclosed. The main advantage of this configuration is that it has an elongated body similar to that of traditional lancet 46 (shown in FIG. 3) making it easy to hold and manipulate, but this long dimension is oriented perpendicular to the lancing axis, thereby contributing to the previously stated goal of making device 10 low profile in height. The body of lancet 89 should be flat or keyed to allow the lancet holding mechanism to keep sharp 50 oriented properly with the lancing axis. Lancet 89 can be driven downward in a pure vertical translation along a straight lancing axis, or it can be rotated about a horizontal axis such that sharp 50 travels in an arc and becomes perpendicular to the patient's skin just as it punctures the skin.

Lancet Retention and Ejection

Referring to FIG. 8, the mechanism by which a disposable lancet 76 is retained within the plunger portion 91 of the integrated device lancing subsystem is shown. Lancet body 77 is generally flat and has a notch 92 on each edge for receiving barbs 94 on the plunger's flexible retaining arms 96.

The angles of the lancet's notches 92 and the arms' barbs 94 are chosen to draw lancet 76 into the plunger.

To eject lancet 76, the lancing subsystem mechanism urges lancet 76 out of plunger 91, forcing retaining arms 96 to flex outward. Once lancet 76 has moved far enough, barbs 94 bear on the tapered tail 98 of lancet 76 and their inward force translates to a longitudinal displacement of lancet 76—they will cause lancet 76 to eject.

The mechanism may use a linear plunger to eject the lancet (pushing in the downward direction in FIG. 8), or a wedge that bears between some feature on lancet and the plunger body. For instance, to further reduce the height of plunger mechanism 91, a wedge-shaped eject lever could extend perpendicularly into the plane of FIG. 8 and contact rear tapered edge 100 to urge lancet 76 downward and out of device 10. Preferably, an interlock mechanism is incorporated so that lancet 76 cannot be ejected while cap 38 is still in place. Alternatively, the ejection lever can be located inside cap 38 to achieve this same result.

Strip Loading Protected from Sharp

Referring again to FIG. 3, loading of test strip 42 will now be discussed. In the compact integrated device 10, test strip 42 and sharp 50 are located fairly close together. In order to eliminate the likelihood of the user accidentally sticking himself on the lancet sharp 50 while inserting a test strip 42, integrated device 10 is arranged so that a test strip 42 can be inserted without removing the protective cap 38 from head 34 of the device.

Cap 38 covers the lancet sharp 50 at all times and is removed only to replace the lancet 46. Test strip 42 is inserted into a slot 102 in lower housing shell 30 on the outside of cap 38, and the device mechanism moves strip 42 from this loading position into the interior of cap 38 and to the testing position near lancet sharp 50. The same mechanism moves test strip 42 away from sharp 50 and returns it to the load position for disposal after a test.

Test Strip Trajectory

Referring to FIGS. 9A and 9B, strip trajectories will be discussed. One of the biggest challenges in developing an automated, integrated device is creating an autonomous mechanism that can introduce a test strip 42 into a small blood sample and get an acceptably high rate of successful fills (blood entering test strip test chamber). Laboratory experiments indicate that the trajectory along which strip 42 moves into contact with the blood droplet 104 has a significant effect on this success rate.

Referring to FIG. 9A, initial experiments held a test strip 42 at a 65° angle to the sample platform 106, and moved strip 42 along a straight line perpendicular to platform 106. The edge 108 of strip 42 entered droplet 104 from above and stopped moving once it contacted the sample substrate (a glass slide). This arrangement produced erratic fill rate results, and showed a limited acceptable range of mislocation tolerance between droplet 104 and the strip 42 nominal location, as shown in FIG. 9C.

Referring to FIG. 9B, in subsequent experiments the test fixture was modified so it held test strip 42 at a 35° angle and moved it along a 25 mm radius arc whose axis was parallel to strip 42 and sample platform 106. The axis location was chosen so that edge 108 of strip 42 was tangent to sample platform 106 at the lowest point of the trajectory. When in use, strip 42 would be moving approximately parallel to and touching the surface of the sample substrate as fill channel 44 on strip edge 108 contacted droplet 104. This trajectory provides much more consistent results and a higher successful fill rate, as well as a significantly larger tolerance for mislocation, as shown in FIG. 9D. It is believed that the wider tolerance is due to the "squeegee" action of this trajectory, as it tends to scrape blood off the substrate and push it along in front of strip 42 until strip 42 stops moving.

Referring to FIGS. 12 and 13, a test fixture demonstrating an alternative strip trajectory is disclosed. In this mechanism, one end of test strip 42 is received within electrical connector 120 which is attached to mount block 122. Mount block 122 is slidably attached to pivot arm 124, which in turn is pivotably attached to base plate 126 with pivot bolt 128. Compression spring 130 biases mount block radially outward from pivot bolt 128. Guide pin 132 is attached to mount block 122 and travels in cam slot 134 formed in base plate 126, causing spring 130 to compress as mount block 122 and guide pin 132 travel from left to right along cam slot 134. Torsion spring 136 mounted on pivot bolt 128 drives pivot arm 124 counter-clockwise when release pin 138 is pulled from hole 140 in pivot arm 124, such as by an electric solenoid, motor, or manual release lever.

The trajectory of strip 42 in this embodiment is controlled by cam slot 134. It can be seen that the right end of cam slot 134 has a portion 142 that angles downward just before a short horizontal portion 144 at the right extremity. Angled portion 142 yields a strip trajectory that prevents device cap 38 from having a knife-like edge along the slotted opening where test strip 42 partially emerges from cap 38 to contact the patient's skin. Short portion 144 allows strip 42 to squeegee along the patient's skin before it comes to rest. In the preferred embodiment, this travel distance along the skin is about 1 mm. Making this distance longer increases the risk that strip 42 may possibly be impeded by a skin irregularity, such as a raised mole. Making this distance shorter increases the risk that strip 42 lands directly on sample 104 and does not capture the entire sample when moving along the skin. In the preferred embodiment, strip movement mechanism 160 is designed to have test strip edge 108 come to rest in the center of sample 104, with tolerances such that edge 108 may undershoot the sample center by 0.005 inch and may overshoot it by 0.010 inch.

In this embodiment, the remainder of cam slot 134 (to the left of angled portion 142) is not an arc concentric with pivot bolt 128 because it is desirable to have the test strip loading location farther to the left of the lancing location to allow sufficient room for the user's fingers to insert the strip. This non-concentric slot 134 is the reason for the slidable, spring loaded arrangement between mount block 122 and pivot arm 124.

Other strip angles and trajectories can be alternatively used, keeping in mind that strip fill performance is improved when the strip approaches the target sample from the side. Also, good machine design practice dictates that the maximum pressure angle (the angle between a line drawn from the axis of rotation to the point of contact, and a line orthogonal to the cam surface at the point of contact) be no more than 30°. In other alternative embodiments, the entire strip need not be moved. For instance, the proximal end of strip 42 can be held stationary while the distal end is deflected away from and/or toward droplet 104 with cams, rollers, guides or other suitable devices. Or, as shown in FIGS. 16A, 16B, 17A, 17B, or 18, the strip can be translated in a vertical or inclined line and the squeegee action can be accomplished by a compliant member such as a leaf spring or compression spring. Alternatively, the distal end of strip 42 may follow a helical path as the proximal end is simultaneously lowered and rotated (not shown.)

Strip Guiding and Location Control

To aid in aligning test strip 42 more precisely in its longitudinal direction with the target blood droplet, connector 120 is preferably biased outwardly when in the strip loading position (as shown in FIG. 12) and allowed to be urged inwardly in the direction of arrow A as mount block 122 travels to the blood acquisition position. This can accomplished by wave washers between pivot bolt 128 and pivot arm 124, or by other compliant measures such as flexure 146 formed in mount block 122. As mount block 122 moves downwardly, cam surface 148 on its distal end can contact a mating feature on device cap 38 to move test strip longitudinally into a known and repeatable position. In this manner the number of parts requiring closely controlled tolerances on their interfaces for this longitudinal positioning can be limited to strip 42, connector 120, mount block 122 and cap 38, instead of a whole chain including the above parts and others having moving interfaces such as pivot arm 124, pivot bolt 128, base plate 126, upper housing shell 28, lower housing shell 30, etc., which would create a much larger tolerance stack-up and increase costs of fabrication and assembly. Preferably, the cam surface 148 could be located directly on connector 120 to further eliminate the tolerances associated with mount block 122.

Referring to FIG. 10, additional strip guiding features are disclosed. Not only should the integrated automated system have good control over the lancing site location as described above, it should also tightly control the location of the test strip fill channel 44. To accomplish this, integrated device 10 has a carefully sized channel 110 that serves to guide test strip 42 from its load position down to the test site and locate it exactly with respect to the lancing site. During strip motion, channel 110 can even ensure that strip 42 is fully seated in its connector by gradually reducing lengthwise clearance along the travel path. Once strip 42 approaches the test position, its critical edge 108 can be spring-loaded to register against surface 112 inside cap 38 that tightly controls its location with respect to the lancet guide bore 60.

In the preferred embodiment shown, guide channel 110 and registration surface 112 for test strip 42, guide bore 60 for lancet 46, and a registration surface for contacting cam surface 148 on mount block 122 or connector 120, are all molded into the same single part (protective cap 38). This allows tight control of the dimensional relationship between these features by reducing the tolerance stack-up between them and gives the best opportunity of ensuring that strip 42 will contact blood droplet 104.

Variable Strip Approach Timing

In order for the above-described strip approach to succeed, blood sample 104 should be present on the skin before strip 42 moves into position. Since human physiology varies such that it cannot be predicted exactly how long after lancing an appropriate-sized droplet will appear on the patient's skin, integrated device 10 preferably can be adjusted by the user to account for this variation.

In the preferred embodiment of integrated device 10, a processor-based electro-mechanical system controls the amount of time that elapses between firing of the lancet and the approach of test strip 42 to the test site. Patients who bleed easily can adjust this duration to be relatively short (for example 5 seconds) and those who bleed slowly can adjust it to be longer (for example 20 seconds.) Alternatively, a purely mechanical system for this adjustable delay may be used.

This adjustability allows the total integrated device test time to be as quick as possible, not burdening all patients with a fixed wait time long enough for those who bleed slowly.

Strip Motion/Cap Removal Interlock

Referring to FIG. 11, a cap removal interlock will be discussed. In order to protect the strip handling mechanism and ease changing of lancet 46, strip 42 should be returned to its loading position before the user removes cap 38. The preferred embodiment of integrated device 10 ensures this by combining strip return and cap removal into a single user-operated control. This control is a sliding button 40 that runs in an L-shaped slot 114. To return strip 42 from the testing position to the load/unload position, the user slides button 40 along the long leg of L-slot 114, as shown by arrow B. To remove cap 38, the user slides button 40 along the long leg of L-slot 114 and then pushes it into the short leg of slot 114. This way the user is forced to return strip 42 to the load/unload position before he can remove cap 38.

Test Strip Ejection

Traditional blood glucose testing utilizing a test strip 42 requires touching one end of strip 42 to the blood sample of interest. Once the test is complete, the bloodied test strip 42 needs to be disposed of. For health and safety reasons, it would be preferable not to require the user to handle used strips 42 after testing. Accordingly, a strip-eject mechanism can be employed on integrated device 10 that allows the user to remove a used strip 42 from device 10 without touching the strip. This mechanism can use pinch-rollers to drive strip 42, a plunger to push strip 42 out of its connector, or similar well-known mechanism.

Overall Operation

Referring mainly to FIG. 1, the overall operation of integrated device 10 to measure blood glucose will be described. The patient first pushes cap removal lever 40 over and up along L-shaped slot 114 to remove device cap 38. If a used lancet 46 still remains in lancet holder 68, ejection lever 36 is pushed downward to eject lancet 46 for disposal. Preferably the ejection mechanism is designed such that it cannot be actuated while device cap 38 is still in place. A fresh lancet 46 is inserted into lancet holder 68, and lancet cap 51 is removed. Lancet holder 68 should be designed such that it provides a retention force that is greater than the force required to separate cap 51 from lancet 46, so that lancet 46 is not pulled from lancet holder 68 when the patient tries to remove cap 51. Device cap 38 is then reinstalled on device 10. Alternately, cap aperture 54 and lancet cap 51, 78, 80 or 84 can be sized such that device cap 38 can be reinstalled before the lancet cap is removed from the lancet.

The patient next removes a fresh test strip 42 from its desiccated vial and inserts the proper end into a mating connector (not shown) within slot 102 in device housing 26. Preferably test strip 42 includes a conductive bar across an outer face such that the insertion of strip 42 powers on device 10. Instructions guiding the patient through the testing process can be displayed on LCD 16. Alternately, function button 12 can be used to turn on device 10.

With a fresh lancet 46 and test strip 42 loaded, integrated device 10 is cocked by pulling up on cocking collar 22, and then placed over the test site on the patient, with recess 52 of cap 38 resting on the skin. Preferred testing sites include the forearm, upper arm, outer thigh, calf, and around the base of the thumb. Once device 10 is positioned, the patient presses actuator button 20 which causes lancet 46 to drive downward penetrating the skin and then retract. After a predetermined and preferably user-settable delay for allowing blood to emerge from the lancing site on the skin, test strip 42 is brought down along an arcuate path into contact with the blood sample. The patient holds device 10 in this position until device 10 emits an audible and/or visual indication that a sufficient amount of blood has been drawn into fill channel 44 of test strip 42 (detected by electrical measurements on strip 42.) Device 10 then performs the appropriate measurements on the electrochemical process within test strip 42, and when complete displays the result on LCD 16. Further manipulation of data or settings can be performed by pressing function buttons 12 and 14.

After a test is complete, lever 40 is pushed towards the short leg of L-shaped slot 114 to return used strip 42 to the load/ unload position outside of protective cap 38. Strip 42 can then be removed from device 10 for disposal by pressing a strip eject lever or by manually removing strip 42. Used lancet 46 can also be removed at this time for disposal, as previously described.

Control Solution Test Scheme

Occasionally testing needs to be performed with a fresh test strip 42 and a "control solution" instead of blood to ensure that device 10 is calibrated and working properly. For this procedure, the patient uses function button 12 and/or 14 to indicate to device 10 that a control solution test will be performed. Cap 38 is removed, either before or after a fresh test strip 42 is inserted into device 10. To avoid risk of accidental lancing, lancet 46 is preferably capped or removed during this process. With cap 38 out of the way and test strip 42 in the load/unload position, a drop of control solution can be applied to fill channel 44 of test strip 42. This test proceeds much like the blood glucose test described above, but strip 42 is never moved from the load/unload position and lancet 46 is never fired. After the control solution test, test strip 42 is ejected and cap 38 is replaced.

Fill Channel Location Coding

Referring to FIG. 14, a scheme for encoding test strips 42 with fill channel 44 location data is disclosed. In the manufacture of disposable test strips such as for testing blood glucose, it can be difficult to produce large quantities of strips 42 all having their fill channels 44 located a predetermined distance from an end of the strip 42 within a narrow tolerance. Since the blood samples 104 to be acquired by strips 42 are becoming quite small (e.g. 0.050 inches in diameter), a wide fill channel location tolerance can make it difficult or impossible for an integrated testing device to automatically align the test strip 42 with the blood droplet 44. This problem can be solved by providing integrated device 10 with a motor or other prime mover to position the strip 42 longitudinally, and encoding the fill channel location for each strip 42 in a calibration code specific to that strip or batch of strips. When the calibration code is entered by the user or detected from strip 42 automatically, device 10 can then position the test strip 42 accordingly.

Currently, many disposable test strips are sold with a code to calibrate the meter to the electrochemistry found on that particular test strip. This calibration code can be, for example, one of four numbers. If the fill channel location is characterized and similarly categorized as being within one of four possible ranges, it can be assigned one of four letters. The number and letter calibration codes can be merged together to form a 4 by 4 array. In this way, one of 16 different numbers can be used for each test strip, with each number uniquely identifying the electrochemistry calibration and fill channel location.

As shown in FIG. 14, the user enters a calibration code, which includes positional data, via the user interface 150. Microprocessor 152 then reads data from an EEPROM 154 which indicates how far to advance motor 156 to align fill channel 44 to the target droplet 104. Home sensor 158 can be used to provide a location reference.

Shape Memory Alloy Firing Mechanism

Referring to FIG. 15, an alternative method for firing lancing mechanism or strip delivery mechanism is disclosed. In the preferred embodiment of integrated device 10, the lancing or plunger mechanism 91 (shown schematically in FIG. 8) is cocked by pulling up on cocking collar 22, and fired by pressing actuator button 20 (both shown in FIG. 1.) The test strip moving mechanism 160 (shown in FIGS. 12 and 13), on the other hand, is not directly actuated by the user but is instead controlled by the device's microprocessor 152, which ensures a suitable delay between lancet firing and test strip movement as described above. An electric solenoid can be employed between microprocessor 152 and release pin 138, but given the typical force required to move pin 138, the size of the solenoid and the batteries required to drive it is unwieldy. Since pin 138 does not need to be extracted with great speed, a motor and lead screw arrangement can be employed instead of a solenoid, but this introduces complexity, cost and reliability issues. To overcome the above drawbacks, a shape memory alloy (SMA) wire can be used to drive release pin 138.

In the preferred embodiment shown, a Nickel-Titanium alloy, know as Nitinol, is used in the shape of a wire 162. At room temperature, a nitinol wire can easily be stretched 3-5% beyond its fabricated length. Upon heating the wire above a certain temperature threshhold, the wire will return to its fabricated length with some force. At the time test strip 42 is to be moved, microprocessor 152 on printed circuit board 164 initiates a current through anchor post 166, which passes through wire 162 and returns to PCB 164 through a chassis ground. The current heats up Nitinol wire 162, causing it to contract to its original length. The shortened length of wire 162 pulls release pin 138 in the direction of arrow C against the force of compression spring 168 located between base plate 126 and stepped shoulder 170 on pin 138. When the end of pin 138 moves enough to disengage from hole 140 in pivot arm 124, test strip moving mechanism 160 moves the test strip as previously described. When the current running through wire 162 is shut off, wire 162 cools and is again stretched by the compression spring 168. This allows spring 168 to push pin 138 back out again (opposite the direction of arrow C) to engage pivot arm 124 when arm 124 is returned to the raised position.

Ferules 172 or clamps are preferably crimped onto ends of wire 162 to provide attachment points. To vary the forces and contraction lengths achieved by Nitinol wire in a small space and to perhaps make electrical connections easier, each end of the wire can be connected to its own post 166 on PCB 164, and the wire can be run through a small, insulated pulley connected to the end of pin 138. Additional pulleys or turning points can be attached or formed within the device housing. In another alternative embodiment, electrical connectivity can be provided to the wire by attaching electrical wires near the ends instead of passing the current through the anchor points. Shapes other than wire, such as a rod, bar, sheet or coil can be used. Nitinol or other shape memory alloys can be used to provide a tensile or compressive force to move pin 138. Alternately, a piezoelectric material can be used.

The preferred embodiment of integrated device 10 will have a specified operating temperature range, for example between 0 and 40 degrees Celsius. To ensure that wire 162 reaches the proper temperature to contract and operate the release mechanism properly when device 10 is anywhere within the specified temperature range, conventional control circuitry would always apply the maximum electrical current required to heat the wire from the bottom of the temperature range to the temperature required for wire contraction. However, device 10 would typically not be operated at the bottom of the predetermined operating range, so much of the current applied to wire 162 during each use would merely be drained from the device's batteries without providing any benefit. To overcome this drawback, device 10 should utilize a temperature sensor (which can also be used for other testing functions) and a current switching circuit that supplies only enough current to elevate wire 162 from the ambient temperature to the contracting temperature. Rather than supplying a constantly decaying current from a charged capacitor to wire 162, the device's microprocessor can be configured to sense the ambient temperature and control a switch with one of its outputs to provide a series of pulses of current to wire 162 to cause its contraction. As ambient temperature decreases, the microprocessor provides pulses of longer duration, approaching a constant source of current as the ambient temperature approaches the bottom of the predetermined operating range. Alternatively, rather than pulsing the current, the duration of the current can be controlled based on the ambient temperature (i.e. a shorter duration for a higher ambient temperature.) By employing this inventive circuitry, smaller batteries can be used and/or longer battery life can be achieved, thereby making device 10 more compact and less expensive.

The invention has been described with reference to various specific and preferred embodiments and techniques. However, it will be apparent to one of ordinary skill in the art that many variations and modifications may be made while remaining within the spirit and scope of the invention.

The invention claimed is:

1. A method for sampling and testing an analyte comprising:
   placing an integrated sampling and testing device on a test site of a patient, wherein the integrated device comprises:
      a housing defining at least a first aperture;
      a lancing device comprising a lancet; and
      a test strip;
   performing a single operation of the integrated device to:
      advance and withdraw the lancet through the first aperture to pierce skin of the patient to express blood at the test site without application of a vacuum to the test site through the first aperture; and
      advance the test strip from a first position to a blood sample contacting position wherein the advancing of the test strip comprises moving at least a portion of a strip movement mechanism in an arcuate trajectory;
   contacting the test strip to the expressed blood at the test site to receive a submicroliter sample of the blood to perform analyte testing on the blood sample; and
   displaying a result corresponding to the analyte testing.

2. The method of claim 1, wherein the performing the single operation comprises depressing a button of the device.

3. The method of claim 1, wherein the submicroliter sample is of about ⅓ microliter in volume.

4. The method of claim 1, wherein the analyte is glucose.

5. The method of claim 1, wherein the analyte is a ketone.

6. The method of claim 1 further comprising cocking the lancet for piercing.

7. The method of claim 6, wherein the cocking comprises pulling on a mechanism of the device.

8. The method of claim 1, wherein the test strip is moved along an axis substantially perpendicular to the test site.

9. The method of claim 1, wherein the test strip is moved along an axis substantially parallel to the lancet.

10. The method of claim 1, wherein the lancet is spring biased.

11. The method of claim 1, wherein the lancing device comprises a driving spring for driving the lancet.

12. The method of claim 11, wherein the lancing device further comprises a retracting spring for retracting the lancet.

13. The method of claim 12, wherein the driving spring and retracting spring are concentrically positioned about the lancet.

14. The method of claim 10, wherein the spring-biasing is accomplished with a torsion spring.

15. The method of claim 1, wherein the lancet and the test strip are displaced from the device in parallel axes.

16. The method of claim 1, wherein the housing further defines a second aperture, and the test strip advances to the blood sample contacting position through the second aperture.

* * * * *